United States Patent [19]
Tidwell et al.

[11] Patent Number: 5,202,320
[45] Date of Patent: Apr. 13, 1993

[54] METHOD FOR TREATING LEISHMANIASIS

[76] Inventors: Richard R. Tidwell, 101 Forest Ridge Dr., Chapel Hill, N.C. 27514; J. Dieter Geratz, 713 Kenmore Rd., Chapel Hill, N.C. 27514; James E. Hall, 2440 Springview Trail, Chapel, N.C. 27514; Dennis E. Kyle, 9415 Curran Rd., Silver Spring, Md. 20901; Max Grogl, 3404 Tan Terra Cir., Brookville, both of Md. 20833; Kwasi A. Ohemeng, 112 Overlook Dr., Clinton, N.J. 08809

[21] Appl. No.: 334,730

[22] Filed: Apr. 6, 1989

[51] Int. Cl.$^5$ .................. A61K 31/55; A61K 31/505; A61K 31/415; A61K 31/155
[52] U.S. Cl. ................... 514/218; 514/256; 514/402; 514/636
[58] Field of Search ............... 514/636, 218, 256, 402

[56] References Cited
PUBLICATIONS

*Reviews of Infectious Disease*, vol. 10, No. 3 pp. 576–577.
*Experimental Parasitology*, vol 52, p. 404–413 (1981).

Primary Examiner—Jerome D. Goldberg
Attorney, Agent, or Firm—W. Dennis Drehkoff

[57] ABSTRACT

This invention relates to a method for treating leishmaniasis which comprises administering to an afflicted host patient, a therapeutically effective amount of a compound having the following structure;

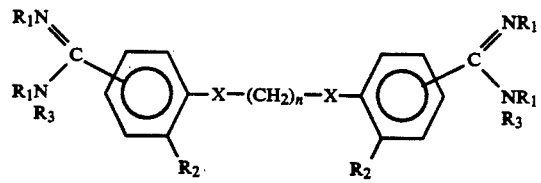

wherein X is O or NH; $R_1$ is H or two $R_1$ of the same amidine group together represent $-(CH_2)_m-$ wherein $m=2$, 3 or 4; $R_2$ is H, $NH_2$, $OCH_3$, Cl or $NO_2$; $R_3$ is H, $CH_3$ or $CH_2CH_3$ and $n=2-6$ or a pharmaceutical acceptable salt thereof provided that X is O both $R_2$ and both $R_3$ cannot be H.

1 Claim, No Drawings

METHOD FOR TREATING LEISHMANIASIS

This invention was made with government support under NO1-AI-72648 awarded by the National Institutes of Health. The government has certain rights in the invention.

GOVERNMENT RIGHTS

The invention described herein may be manufactured and used by or for the government, for governmental purposes, without the payment of any royalties thereon or therefore under certain specific conditions.

BACKGROUND OF THE INVENTION

This invention relates to a method for treating leishmaniasis, caused by Leishmania.

Leishmania are well know intra-cellular protozoan parasites which may give rise to serious infections in man. The organisms are transmitted by the "bite" of an infected sandfly, and invade the reticuloendothelial system (RES). The parasites are highly successful in their ability to grow and multiply in the very tissues of the vertebrate host which are responsible for reaction to invading organisms. Expectedly, such location of Leishmania renders difficult a satisfactory approach to chemotherapy, and there is highly complex inter-play between parasites and cellular immune responses of the host. In the RES, the parasites lie within the host macrophage for at least part of their life cycle. Fusion of host cell secondary lysosomes with the parasitophorous vacuoles apparently occurs without preventing subsequent multiplication of the Leishmania. Such fusion may provide means for access for nutrients to the parasite, but also exposes the parasite to host antibodies and lysosomal enzymes.

In man, the result of successful invasion of the spleen and liver by Leishmania donovani most frequently is death. Scarring of the skin may be the sole manifestation of infection with Leishmania tropica and allied dermatotropic organisms (as, Leishmania aethiopica, L. mexica, L. peruviana, and L. guyanensis). Intermediate in severity are invasions of muco-cutaneous tissues by Leishmania braziliensis. Unfortunately, relatively few drugs have been found to show appreciable anti-leishmanial activity on screening, and fewer yet have merited trial in man. Antimony drugs are a mainstay for treatment, yet severe toxic side effects may occur, in particular, among poorly nourished patients. Of the antimonial drugs, one widely used in the clinic is the N-methyl glucamine salt of antimonic acid, frequency called meglumine antimonate. Toxicity of such drugs may affect the liver (hepatitis), kidneys (nephritis), or the heart (myocarditis). Of these toxic effects, myocarditis is the greatest and most common problem.

Pentamidine has been known for decades and was originally shown to be useful for the treatment of trypanosomiasis. Of more recent time, pentamidine has been found to be extremely useful in the treatment of Preumocystis carinii pneumonia, especially in immunocompromised patients suffering from the acquired immunodeficiency syndrome (AIDS). Pentamidine has been shown to have limited utility for the purpose of treating leishmaniasis as indicated in Reviews of Infectious Diseases, Vol. 10, Number 3, pages 576–577 and Experimental Parasitology, Vol. 52, page 409 (1981).

In view of the lack of a satisfactory agent for the treatment of leishmaniasis, a need exists for a more-effective anti-leishmanial agent having good therapeutic properties.

SUMMARY OF THE INVENTION

Surprisingly, it now has been discovered that leishmaniasis may be treated with pentamidine analogues. Accordingly, the present invention provides a method for treating leishmaniasis which comprising administering to an afflicted host a therapeutically effective amount of compound having the structure of formula I:

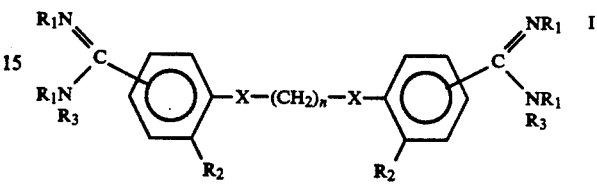

wherein X is O, NH or S; $R_1$ is H or two $R_1$ groups on the same amidine group together represent $-(CH_2)_m-$, wherein $m = 2, 3$ or $4$; $R_2$ is H, $NH_2$, $OCH_3$, Cl, or $NO_2$; $R_3$ is H, $CH_3$ or $CH_2CH_3$ and $n = 2-6$, or pharmaceutically acceptable salts thereof, or more preferably a compound of formula II:

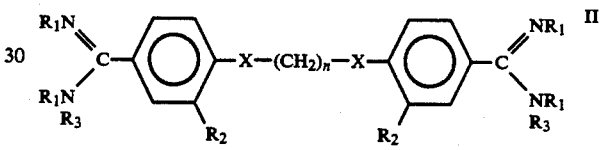

wherein X, $R_1$, $R_2$, $R_3$, m and n have the foregoing meanings, or a pharmaceutically acceptable salt thereof.

DETAILED DESCRIPTION OF THE PREFERRED EMBODIMENTS

The present invention provides a new method for treating leishmaniasis by administering compounds of formula I, above, or pharmaceutically acceptable salts thereof. Formula I encompasses pentamidine, along with various analogues or derivatives thereof, all of which are aromatic diamidines.

Obviously, the therapeutically effective dosage of any specific compound will vary somewhat from compound to compound and patient to patient. As a general proposition, a dosage from about 0.1 to about 20 mg/kg will have therapeutic efficacy. However, toxicity concerns at the higher level may restrict the dosage to a lower level such as up to about 10 mg/kg, based upon the weight of free-base. Typically, a dosage from about 0.5 mg/kg to about 5 mg/kg will be employed. The duration for the treatment is usually once per day for a sufficient length of time for the patient to become asymptomatic. Depending upon the severity of the infection in the individual patient, this may last anywhere from two to three weeks, or longer.

In accordance with the present method, a compound of Formula I (or preferably of Formula II), or a pharmaceutically acceptable salt thereof, may be administered orally as a solid, or may be administered orally, intramuscularly, or intravenously, as a solution, suspension, or emulsion. Alternatively, the compound or salt may also be administered intravenously or intramuscularly as a liposomal suspension. Further, the compound, if hydrophobic, may be administered in an encapsulating hydrophilic liquid which can essentially encapsulate the hydrophobic compound.

Most often, the pharmaceutical compositions useful in the present invention will comprise a compound of Formula I (or preferably of Formula II), or a pharmaceutically acceptable salt thereof, in any pharmaceutically acceptable carrier. If a solution is desired, water is the carrier of choice with respect to water-soluble compounds or salts. With respect to water-insoluble compounds or salts, an organic vehicle, such as glycerol, propyleneglycol, polyethyleneglycol, or mixtures thereof, may be suitable. In the latter instance, the organic vehicle may contain a substantial amount of water. The solution in any instance should be sterilized in a suitable manner, preferably by filtration through a 0.22 micron filter. The compositions useful in the practice of the present invention may be provided in the form of vials, ampoules, and the like.

In addition to compounds of Formula I (or II), or their salts, the pharmaceutical compositions may contain other additives, such pH adjusting additives, in particular agents such as acids, bases, or buffers, including sodium lactate, sodium acetate, and sodium gluconate. Further, such compositions may contain microbial preservatives, such as methyl paraben, propylparaben, and benzyl alcohol. If a multiple use vial is supplied, the pharmaceutical composition should likewise include such a microbial preservative. The formulations may be, of course, lyophilized, using techniques well known in the art.

When the desired pharmaceutical composition employs a compound of Formula I (or preferably of Formula II), or a salt thereof, which is water-insoluble, the composition may be supplied in the form of an aqueous based emulsion, containing a sufficient amount of a pharmaceutically acceptable emulsifying agent to emulsify the active compound or salt. Particularly useful emulsifying agents are phosphatidyl cholines and lecithin.

Liposomal formulations may likewise be employed in which the compound of Formula I (or preferably of Formula II), or a salt thereof, is either water-soluble, and hence entrapped within the hydrophilic center or pore of the liposome, or is water-insoluble and then substantially entrained within the hydrophobic lipid bilayer which forms the structure of the liposomes. Such liposomal formulations may be reduced in size, as through sonication and homogenization, or may be lyophilized, all using techniques well known to those skilled in the art. Alternative, if the compound or salt is hydrophobic, certain hydrophilic liquids which essentially encapsulate the hydrophobic agent at a molecular level may be employed.

In terms of the present invention, "water-soluble" is meant to define any composition which is soluble in water in an amount of about 50 mg/ml, or greater and the term "water-insoluble" is meant to define any composition which has solubility in water of less than about 20 mg/ml.

The compounds employed in the present invention in general may be synthesized in manners known and readily understood by those skilled in the art. Therefore, there is no need to explain in great detail the methodology used for the synthesis of most such compounds. Further information regarding appropriate synthesis techniques may be taken from copending application Ser. No. 262,535, Filed Oct. 25, 1988, now U.S. Pat. No. 4,933,347.

It has been found that with respect to the practice of the method of the present invention, in treating Leishmania injection with a compound of Formula I (or preferably Formula II), or a pharmaceutically acceptable salt thereof, certain compounds appear to possess superior efficacy to others. Pentamidine, for example, has been found to be moderately effective against Leishmania as have most of the compounds within Formula I (or II above. It was especially surprising to find that the most efficacious products within the scope of the present invention are a compound having a structure as defined by Formula II wherein $X=N$; $R_1$, $R_2$, and as defined by Formula II wherein $X=N$; $R_1$, $R_2$, and $R_3=H$, and $n=5$, and a compound having the structure as defined by Formula II wherein $X=O$; $R_1$, $R_2$ and $R_3=H$, and $n=6$. Both compounds are structurally similar to pentamidine.

The present invention will be further described in accordance with the following non-limiting examples.

EXAMPLES 1-18

Compounds falling within the scope of Formula I (and II) were obtained, having the structures identified in Tables I through III. To test those compounds against Leishmania the following general procedure was employed.

Chemotherapeutic Agents

Pentamidine and the analogs of pentamidine used in this study were synthesized using the procedures detailed in copending application Ser. No. 262,535, Filed Oct. 25, 1988, now U.S. Pat. No. 4,933,347.

In Vitro Screening For Anti-Leishmanial Activity

Leishmania mexicana amazonensis, strain MHOM/BR/73/M2269 (WR669), promastigotes were grown to early log phase in Schneider's Drosophila Medium (GIBCO) supplemented with 20% heat-inactivated fetal bovine serum GIBCO) and 100 ug/ml gentamicin sulfate [Parasitology 76:309 (1978)]. The assay medium was Schneider's plus 10% fetal bovine serum. Serial dilutions of the compounds of use in the present invention were suspended in the assay medium an prepared in duplicate rows of a 96-well microtiter plate. Parasite suspension (200 ul) at $2.5 \times 10^6$ cells/ml was added to each well and each plate was sealed and incubated under air at 25° C. After 24 hours, [methyl-3H] thymidine (20 Ci/mmol) was added to yield 1-2 uCi/well. After an additional 18 hours, the cells were harvested with a Skatron cell harvester onto glass microfiber filters. The filter disks were washed and dried and counted using a Beckman LS3801 scintillation counter. The data on uptake of $^3$H-thymidine was fitted to a logistic-logarithmic concentration response function by a non-linear regression method and the drug concentrations required to inhibit 50% incorporation of $^3$H-thymidine were determined [Antimicrob. Agents Chemother. 16:710 (1979); Exper. Parasitol. 66:86 (1988)]. The results are set forth in Tables I-III.

TEST RESULTS

The results of employing the foregoing procedure to determine the efficacy of compounds within the scope of Formula I (or II) above in treating Leishmania are contained in Tables I-III which show that para-amidines, meta-amidines, and para-imidazolines all have anti-Leishmanial activity. In Tables I and II, $R_1$ and $R_3$ represent hydrogen. Compound Nos. 8 and 9 showed a high-degree of anti-Leishmania activity. Compound 8 is identical to pentamidine except that it has nitrogen atoms in place of the bridging oxygen atoms. Compound 9 (hexamidine) is identical to pentamidine except that it contains one more methylene bridging group.

From Table II it is seen that the meta-amidines are comparable to the para-amidines, although they show a somewhat substantially lessened activity, in comparison with the para-amidines.

From Table III it can be seen that the compounds of Formula II wherein the amidine groups have been converted to imidazolines are as a whole essentially as efficacious as their simple amidine counter-parts.

TABLE I

LEISHMANIASIS MEXICANA AMAZONENSIS vs. PARA-AMIDINES

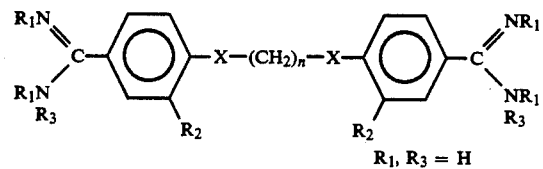

$R_1, R_3 = H$

| EXAMPLE NO. | X | n | $R_2$ | (NEW) $IC_{50}$ (uM) | Rank |
|---|---|---|---|---|---|
| 1 | O | 3 | $OCH_3$ | 1.69 | 10 |
| 2 | N | 4 | H | 0.58 | 3 |
| 3 | O | 4 | H | 1.23 | 7 |
| 4 | O | 5 | H | 0.65 | 4 |
| 5 | O | 5 | $NO_2$ | 2.57 | 13 |
| 6 | O | 5 | $NH_2$ | 2.32 | 12 |
| 7 | O | 5 | $OCH_3$ | 6.53 | 16 |
| 8 | N | 5 | H | 0.35 | 2 |
| 9 | O | 6 | H | 0.33 | 1 |
| 10 | O | 5 | Cl | 1.11 | 6 |

TABLE II

LEISHMANIASIS MEXICANA AMAZONENSIS vs. META-AMIDINES

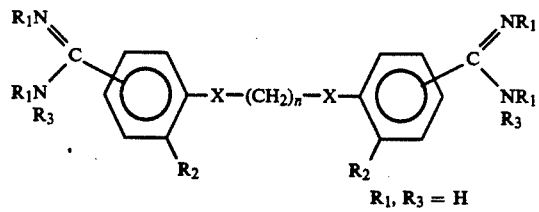

$R_1, R_3 = H$

| EXAMPLE NO. | X | n | $R_2$ | (NEW) $IC_{50}$ (uM) | Rank (of 18) |
|---|---|---|---|---|---|
| 11 | O | 3 | H | 7.20 | 17 |
| 12 | O | 4 | H | 3.28 | 15 |
| 13 | O | 5 | H | 1.66 | 9 |
| 14 | O | 6 | H | 2.92 | 14 |

TABLE III

LEISHMANIASIS MEXICANA AMAZONENSIS vs. PARA-IMIDAZOLINES

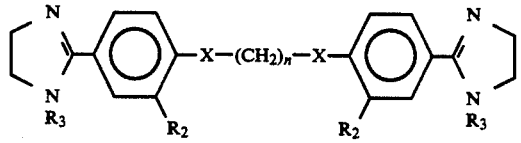

| EXAMPLE NO. | X | n | $R_3$ | $R_2$ | (NEW) $IC_{50}$ (uM) | Rank | (PREVIOUS) $IC_{50}$ (uM) | Rank |
|---|---|---|---|---|---|---|---|---|
| 15 | O | 5 | H | H | 1.06 | 5 | 0.67 | 4 |
| 16 | O | 5 | $CH_3$ | H | 12.2 | 18 | >4.5 | 17–14 |
| 17 | O | 3 | H | $OCH_3$ | 1.71 | 11 | >4.5 | 17–14 |
| 18 | O | 3 | H | H | 1.47 | 8 | — | X |

What is claimed is:

1. A method for treating leishmaniasis which comprises administering to an afflicted host patient, a therapeutically effective amount for treating leishmaniasis of a compound having the structure of the formula I;

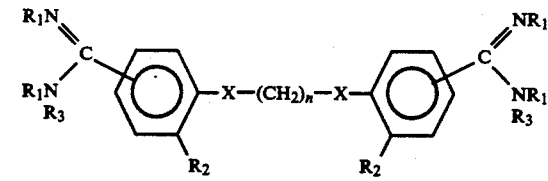

wherein X is O or NH; $R_1$ is H or two $R_1$ of the same amidine group together represents $-(CH_2)_m-$, wherein m=2, 3, or 4; $R_2$ is H, $NH_2$, $OCH_3$, Cl or $NO_2$; $R_3$ is H, $CH_3$ or $CH_2CH_3$ and n=2–6 or a pharmaceutically acceptable salt thereof provided that when X is O both $R_2$ and both $R_3$ can not be H.

* * * * *